United States Patent
Dolling et al.

(10) Patent No.: US 7,326,372 B2
(45) Date of Patent: Feb. 5, 2008

(54) METHOD FOR THE PRODUCTION OF ALKYL LITHIUM COMPOUNDS BY MEANS OF SPRAYING OF LITHIUM METAL

(75) Inventors: Eike Dolling, Goster (DE); Günther Kaletka, Langelshelm (DE)

(73) Assignee: Chemetall GmbH, Frankfurt am Main (DE)

( * ) Notice: Subject to any disclaimer, the term of this patent is extended or adjusted under 35 U.S.C. 154(b) by 485 days.

(21) Appl. No.: 10/503,036

(22) PCT Filed: Feb. 3, 2003

(86) PCT No.: PCT/EP03/01034

§ 371 (c)(1),
(2), (4) Date: Dec. 22, 2004

(87) PCT Pub. No.: WO03/066640

PCT Pub. Date: Aug. 14, 2003

(65) Prior Publication Data

US 2005/0116362 A1    Jun. 2, 2005

(30) Foreign Application Priority Data

Feb. 6, 2002    (DE) ............................... 102 04 680

(51) Int. Cl.
*C07F 1/02*    (2006.01)
(52) U.S. Cl. ................................................. 260/665 R
(58) Field of Classification Search ............. 260/665 R
See application file for complete search history.

(56) References Cited

U.S. PATENT DOCUMENTS

| 2,798,831 A | | 7/1957 | Wilcox |
| 5,332,533 A | * | 7/1994 | Schwindeman et al. 260/665 R |
| 5,776,369 A | | 7/1998 | Dover et al. |
| 5,976,403 A | | 11/1999 | Dover et al. |
| 2003/0096925 A1 | * | 5/2003 | Brockmann et al. ..... 526/123.1 |
| 2004/0251562 A1 | * | 12/2004 | Nakousi et al. ......... 260/665 R |
| 2005/0051911 A1 | * | 3/2005 | Weiss et al. ............ 260/665 R |

FOREIGN PATENT DOCUMENTS

WO    WO-97 06910 A    2/1997

OTHER PUBLICATIONS

Database Compendex OnLine, Engineering Information Inc. NY, Jeppson, et al., Some Safety Considerations . . . Material, & proc of the Seventh Top Meet on the Technol . . . Energy, Reno, NV. USA. vol. 10, Jun. 15, 1986.
Database Compendex "Online,"Engineering Information Inc. NY, Albrecht, et al "Structure and properties . . . alloys", & Proceedings of the 2$^{nd}$ Symposium . . . applications, USA. 1991.

* cited by examiner

*Primary Examiner*—Porfirio Nazario-Gonzalez
(74) *Attorney, Agent, or Firm*—Fulbright & Jaworski L.L.P.

(57) ABSTRACT

A method for the production of alkyl lithium compounds is disclosed, in which metallic lithium is reacted with an alkyl halide in a solvent, whereby the metallic lithium is introduced in the form of lithium particles, generated by spraying molten lithium into an inert atmosphere or into a vacuum.

4 Claims, 3 Drawing Sheets

Figure 1:
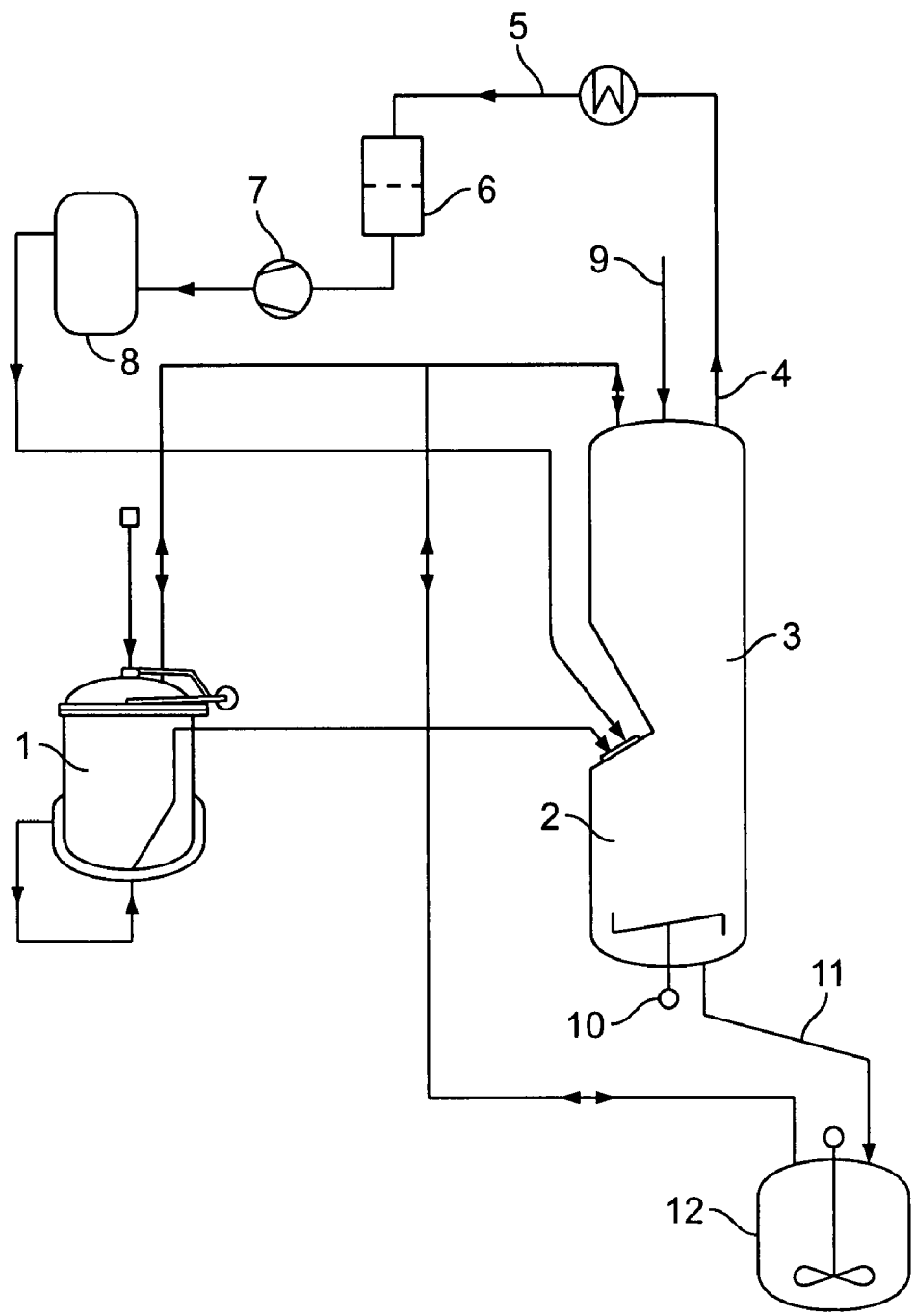

METHOD FOR THE PRODUCTION OF ALKYL LITHIUM COMPOUNDS BY MEANS OF SPRAYING OF LITHIUM METAL

This is a §371 of PCT/EP03/01034 filed Feb. 3, 2003, which claims priority from German 102 04 680.8 filed Feb. 6, 2002, each of which are hereby incorporated by reference in their entireties.

The invention relates to a method of producing alkyllithium compounds, in which lithium metal is atomised to form a lithium dispersion.

Alkyllithium compounds are produced by reacting organic halogen compounds with metallic lithium. Conventionally, the reaction is performed in hydrocarbons or in ethers as solvent.

WO 95/01982 describes in detail the production of alkyllithium compounds from a lithium metal dispersion and alkyl halide, wherein the sodium content of the lithium, the lithium excess relative to the alkyl halide, the alkyl halide, the rate of apportionment, the solvent, the influence of traces of water in the reaction and the reaction temperature are examined. Depending on the solvent, the reaction between lithium and alkyl halide is performed at the boiling point of the solvent of between 50 and 100° C., or between 50 and 125° C. below the boiling point of the solvent.

WO 96/40692 describes a method of producing organolithium solutions, in which cast or extruded lithium rods react with an alkyl halide (e.g. n-, s- or t-butyl chloride) in the molar excess of 3:1 to 20:1 in a solvent under a protective gas atmosphere for 1 to 10 hours with moderate stirring and the product of lithium metal and the secondary product LiCl are separated off in the reactor, In the case of a method variant likewise described in WO 96/40692, no stirring is performed during the reaction (the LiCl formed remains on the Li metal), the product solution is separated off and, once the LiCl has been separated off (e.g. by the addition of solvent, agitation and separation of the LiCl suspension), the excess Li metal is reacted again together with newly added metal in the replenished solvent, with added alkyl halide.

The surface area of the lithium metal has an impact on the activation of the reaction and the subsequent course thereof. A favourable feature is a large lithium surface area. To produce a large lithium surface area, lithium metal is dispersed. During dispersion in an inert fluid, the metal melt is brought to a temperature above the melting point of the metal together with the inert fluid. By applying highly turbulent shear fields, the metal is broken down into small particles. For this purpose, effective agitators such as for example dispersing disks and dispersing turbines, rotor/stator arrangements such as for example Ultra-Turrax, sound or ultrasound generators and other methods. Common to the methods of dispersing lithium metal is the fact that, after production of the dispersion at temperatures above the lithium melting point, the dispersion is cooled to temperatures below the lithium melting point, wherein the lithium particles produced pass into the solid state. So that the dispersed phase produced is maintained, it is conventional to add dispersion auxiliaries, such as oils for example, in the case of lithium particles of small grain size.

As the inert fluid, saturated hydrocarbons are generally used, such as paraffin for example. After cooling, a complex solvent exchange has to be performed when paraffin is used as the inert fluid, during which exchange the dispersing auxiliary is washed out. The solvent exchange is necessary because synthesis of the alkyllithium compounds is performed in lower-boiling solvents. It is also possible to use as the inert fluid for dispersion aliphatic or aromatic hydrocarbons with a lower boiling point than paraffin, such as for example hexane, heptane or toluene. An advantage thereof is that it is then possible to dispense with solvent exchange. However, the melting point of lithium (181° C.), which is above the boiling point of these solvents at normal pressure, requires disadvantageous operation under pressure. In order not to have to raise the necessary pressure range too markedly, particular limits are set for the choice of solvents. A disadvantage here is also the need to remove the dispersing auxiliaries.

The object of the invention is to overcome the disadvantages of the prior art and to provide a method of producing alkyllithium compounds in which lithium metal is used with a very large surface area, wherein, when producing the lithium particles in an inert solvent, the choice of solvent is not restricted and wherein dispersing auxiliaries may be dispensed with.

The object is achieved by a method in which lithium particles are produced by atomisation of molten lithium in an inert gas atmosphere or in a vacuum and the lithium particles are then reacted in a known manner with an alkyl halide in a solvent.

Atomisation of the lithium may be performed with single-fluid pressure nozzles or preferably with two-fluid nozzles. The advantage of the two-fluid nozzle is that the molten lithium is typically present without pressure or at a low overpressure (e.g. 1 to 500 mbar) and is broken down into small metal particles by a propellant jet of inert gas. Argon is preferably used as the inert gas for the propellant jet and/or for the inert gas atmosphere. So that the liquid lithium does not solidify in the nozzle, the nozzle is preferably heated, e.g. by induction heating or heat-transfer oil.

Figure 2:
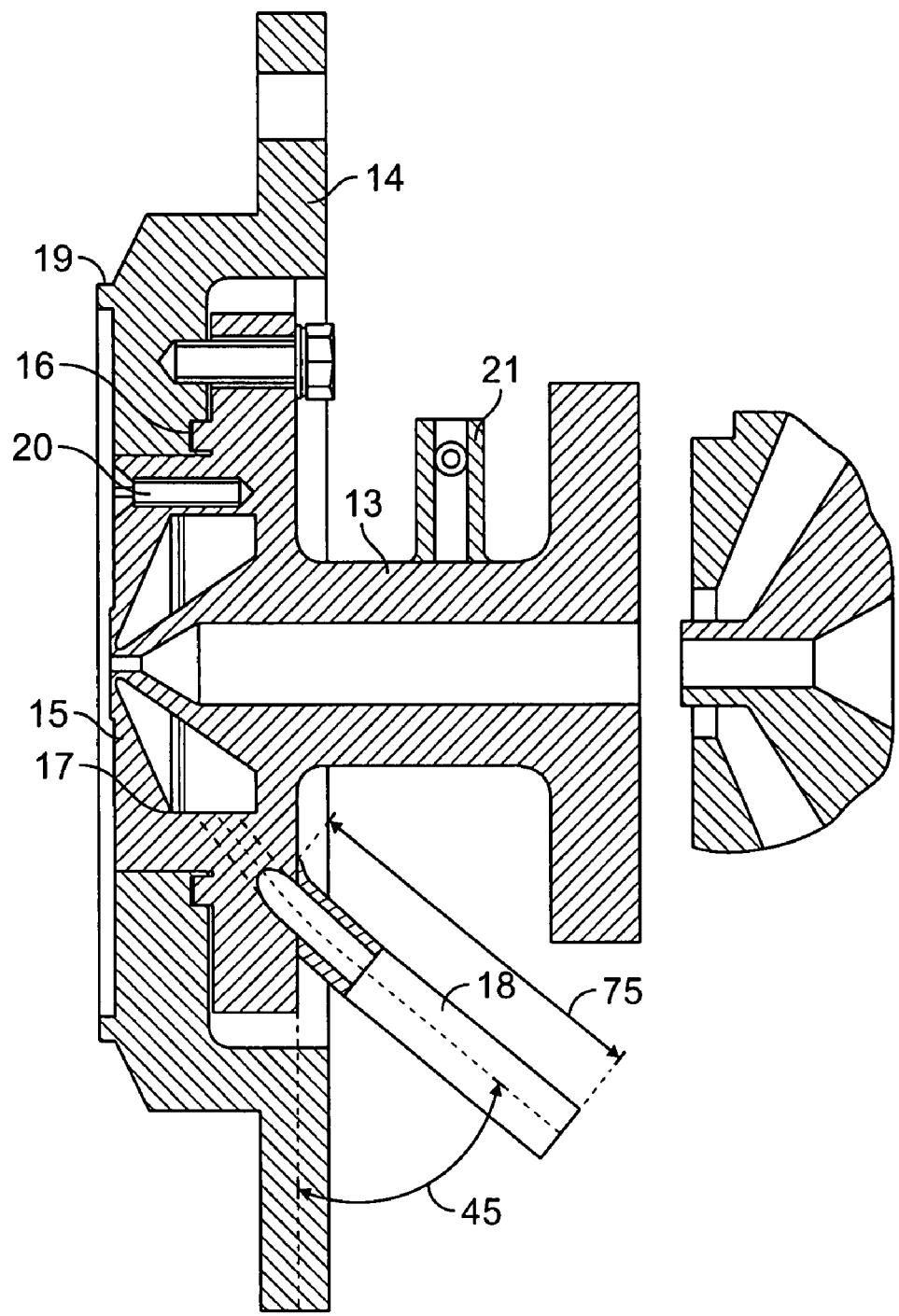
Figure 3:
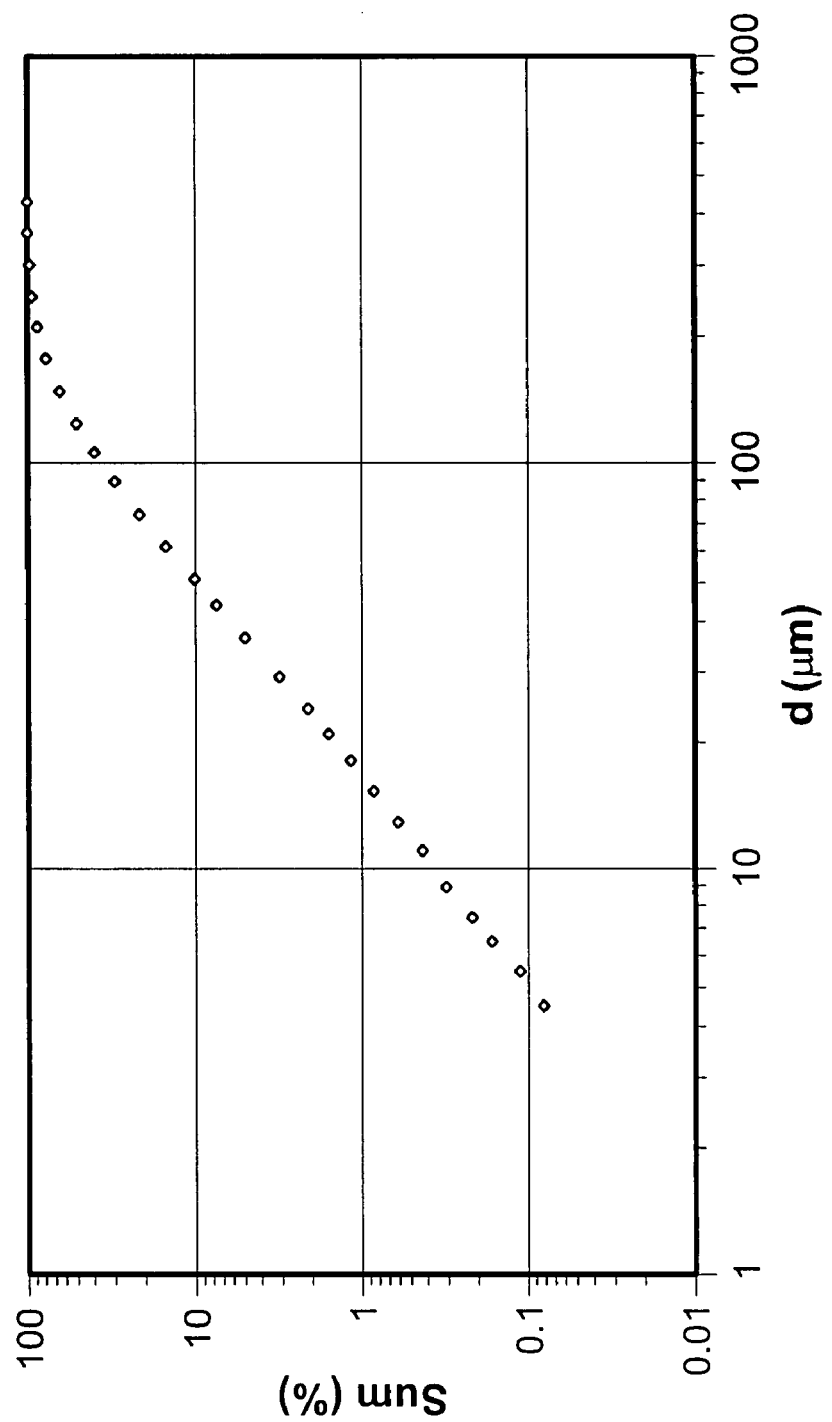

A preferred method is explained in more detail by way of example with reference to FIG. 1, without this constituting any restriction. The lithium is melted in the heated vessel 1 (a preferred temperature range is 190 to 250° C., particularly preferably 200 to 230° C.). The liquid level in the vessel 1 is preferably somewhat lower than the opening of the nozzle 2. This prevents molten lithium from unintentionally running out of the vessel 1. The lithium passes from the vessel 1 into the nozzle 2, where it is atomised in the argon stream into a spray vessel 3. A nozzle is illustrated in FIG. 2. The nozzle preferably overhangs by 0.1 to 1 mm beyond the lithium-conveying central component, particularly preferably by 0.3 to 0.5 mm. The internal diameter of the lithium-conveying central component amounts preferably to 1 to 5 mm, particularly preferably 2 to 4 mm. The argon flows out of the nozzle around the lithium-conveying central component into the spray vessel 3. In this way, a partial vacuum of preferably at least −200 mbar, particularly preferably −500 to −700 mbar, is generated locally at the nozzle opening relative to the pressure in the spray vessel. This partial vacuum at the nozzle opening is sufficient to draw in the molten lithium from the container 1. The greater the selected partial vacuum (this is dependent inter alia on the geometry of the two-fluid nozzle, the admission pressure of the argon, the volumetric flow rate of the argon and the flow velocity of the argon), the less lithium encrustation occurs at the nozzle opening. The admission pressure of the argon amounts preferably to 5 to 10 bar, particularly preferably 7 to 9 bar. The pressure jump at the nozzle opening causes the argon to cool to such an extent that it results in solidification of the lithium which has been atomized into small particles. The average grain size of the lithium particles may be varied by the nozzle geometry, the nozzle diameter and the argon pressure. The lithium particles have average grain sizes (particle diameters) of preferably <300 µm, particularly preferably 50 to 150 µm. Grain sizes of 100 to 130 µm have proven optimum. FIG. 3 shows a typical sum of lithium particle volume (in % of the total volume) as a function of particle diameter d. The grain size is determined by means of laser diffraction (Sympatec Helos instrument made by Sympatec; sensor and evaluation software: Helos; dispersing system: cell; focal length of the focusing lens system: 500 mm; measuring time: 5 seconds; cell pathlength: 21 mm; stirrer speed: 90 rpm). For measurement, a suspension of lithium particles (solvent: hexane) is placed in the cell and stirred with a magnetic stirrer. Measurement is performed in the usual manner with the above-described parameters.

The vessel 1 containing the lithium and the spray vessel 3 are connected together by a pressure compensation line. The lithium particles produced are collected in the spray vessel 3.

The argon is fed via a pipeline 4 from the spray vessel 3 via a cooling apparatus 5 and via a fine filter 6 to the compressor 7 and is intermediately stored in the argon pressure vessel 8, whence it passes back to the nozzle 2. The argon pressure is preferably increased slightly within the system relative to the environment (atmospheric pressure), e.g. by 100 to 500 mbar.

The nozzle 2 is preferably fitted at the level of the middle third of the spray vessel 3. The finest lithium metal particles may thus precipitate out from the argon gas in the chamber positioned above the nozzle, before the argon gas exits from the spray vessel 3 via the pipeline 4.

The lithium particles generated by atomisation may be removed from the spray vessel directly or converted into a suspension by means of a solvent. The lithium particles produced in this way or the lithium suspension produced in this way may be reacted in known manner with an alkyl halide to yield the corresponding alkyllithium compound.

The production of n-, s-, t- and iso-butyllithium is preferred.

An advantage of the method according to the invention is that it does not need any dispersing auxiliary for producing the lithium particles and there is no contamination caused by dispersing auxiliaries. Furthermore, the lithium particles produced by atomisation may be suspended in any solvent customary in the production of alkyllithium. The method is thus not limited to particular solvents and no complex solvent exchange need be performed.

The invention claimed is:

1. A method of producing alkyllithium compounds comprising reacting metallic lithium with an alkyl halide in a solvent, wherein the metallic lithium is in the form of lithium particles which are produced by atomisation of molten lithium in an inert gas atmosphere or in a vacuum.

2. The method according to claim 1, wherein atomisation of the lithium is performed with a single-fluid nozzle.

3. The method according to claim 1, wherein atomisation of the lithium is performed with a two-fluid nozzle.

4. The method according to claim, 3, wherein argon is used to atomise the lithium metal in the two-fluid nozzle.

* * * * *